United States Patent
Arai et al.

(12)

(10) Patent No.: US 6,355,804 B1
(45) Date of Patent: Mar. 12, 2002

(54) PROCESS FOR PRODUCING PIPERIDINECARBOXYLIC ACID AMIDE DERIVATIVES

(75) Inventors: Isao Arai; Takashi Yamamoto; Hirokazu Naora, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/750,243

(22) Filed: Dec. 29, 2000

Related U.S. Application Data

(63) Continuation of application No. 09/415,066, filed on Oct. 12, 1999, which is a continuation of application No. PCT/JP98/01460, filed on Mar. 31, 1998.

(30) Foreign Application Priority Data

Apr. 9, 1997 (JP) ............................................. 9-90564

(51) Int. Cl.$^7$ ..................... C07D 211/06; C07D 411/00; C07D 421/00
(52) U.S. Cl. ........................ 546/196; 546/202; 546/203
(58) Field of Search .................. 546/196, 202, 546/203

(56) References Cited

U.S. PATENT DOCUMENTS

| 5,231,105 A | 7/1993 | Shoji et al. ................ 514/325 |
| 5,932,593 A | 8/1999 | Makino et al. ............. 514/316 |

FOREIGN PATENT DOCUMENTS

| EP | 0 682 015 | 11/1995 | |
| JP | 3-47168 | 2/1991 | .................. 514/316 |
| JP | 8-3135 | 1/1996 | .................. 514/316 |
| JP | 9-176119 | 7/1997 | .................. 514/328 |

OTHER PUBLICATIONS

Kleine et al., *Aminolysis of the Oxazoline Ring of Halomethyl–Substituted Hexahydrooxazolopurines*, Arch. Pharm . . . , 303 (4), pp 378–383, 1970 (with Chemical Abstract).

Iwakura et al., *Reaction of Alkylidenepseudoxazolones with Amines*, Tetraron Letters, No. 45, pp. 5461–5466, 1966 (with Chemical Abstract).

Michael J. Fazio, *Nucleophilic Ring Opening of 2–Oxazolines with Amines: A Convenient Synthesis for Unsymmetrically Substituted Ethylenediamines*, J. Org. Chem., 1984, vol. 49, 4889–4893.

*Primary Examiner*—Alan L. Rotman
*Assistant Examiner*—Raymond Covington
(74) *Attorney, Agent, or Firm*—Oblon, Spivak, McClelland, Maier & Neustadt, P.C.

(57) ABSTRACT

A process for producing piperidinecarboylic acid amide derivatives useful as serotonin antagonists, antithrombocytic agents or intermediates for them, which comprises the step of reacting a 2-oxazoline compound with a piperidine derivative in the presence of an acid is provided. This process is an industrially excellent process for producing piperidinecarboylic acid amide derivatives useful as serotonin antagonists, antithrombocytic agents or intermediates for them.

15 Claims, No Drawings

PROCESS FOR PRODUCING PIPERIDINECARBOXYLIC ACID AMIDE DERIVATIVES

This application is a Continuation of U.S. application Ser. No. 09/415,066, filed on Oct. 12, 1999, now allowed, which is a Continuation of PCT/JP98/01460, filed Mar. 31, 1998.

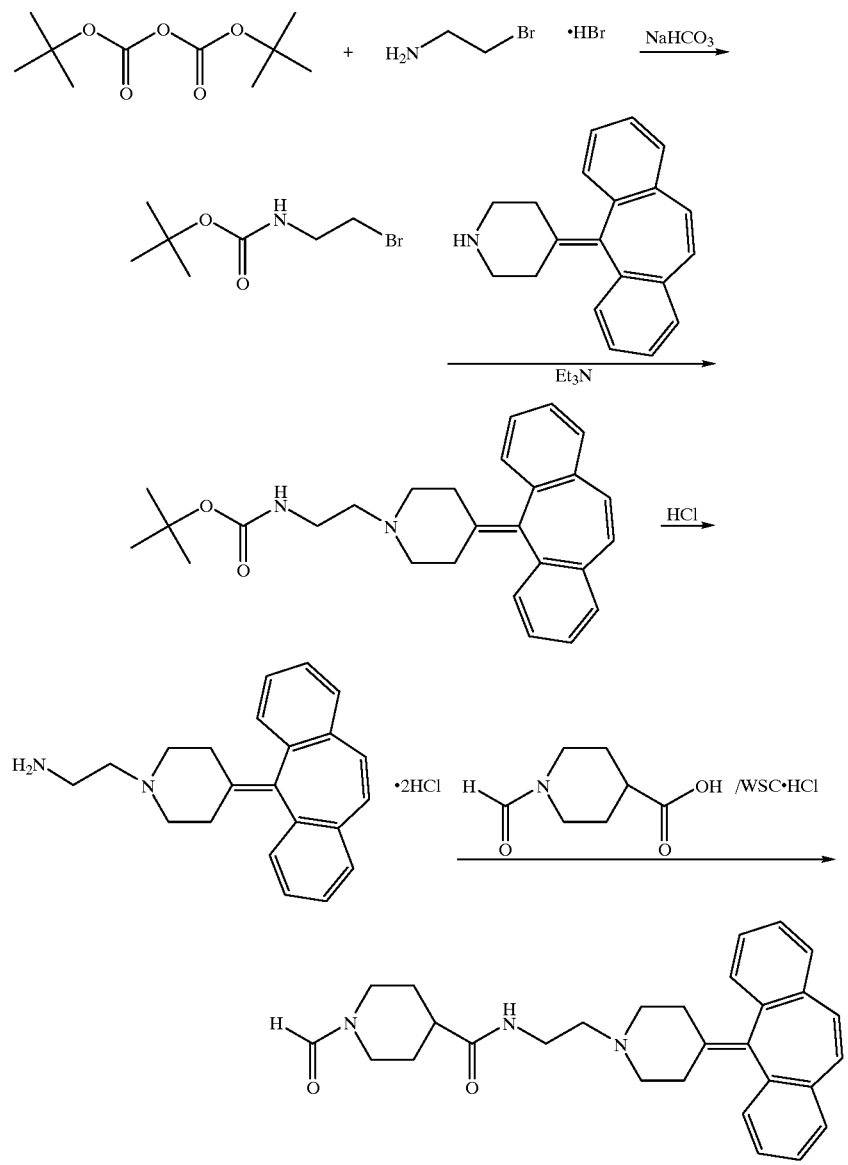

BACKGROUND OF THE INVENTION

The present invention relates to a process for producing piperidinecarboylic acid amide derivatives useful as serotonin antagonists, antithrombocytic agents or intermediates for them.

Ischemic diseases such as myocardial infarction and cerebral infarction are concerned with thrombi. In particular, it is considered that thrombocytes play an important part in the formation of thrombosis in the arteries. Thus, various antithrombocytic agents were developed. For example, Japanese Patent Unexamined Published Application (hereinafter referred to as "J. P. KOKAI") No. Hei 8-3135 reported compounds usable as the serotonin antagonists or antithrombocytic agents. The following process for producing compounds having a piperidinecarboxylic acid amide structure, among those compounds, is disclosed therein.

However, 2-aminoethyl bromide used in this process is a poisonous substance, and carcinogenic aziridine is possible to be formed by the reactions. Thus, this process is not preferred for the production on an industrial scale. Under these circumstances, the development of a safer process has been demanded.

DISCLOSURE OF THE INVENTION

The object of the present invention is to provide an industrially excellent process for producing piperidinecarboxylic acid amide derivatives.

Another object of the present invention is to provide new piperidinecarboxylic acid amide derivatives.

Other objects of the present invention will be apparent from the following descriptions and Examples.

After intensive investigations, the inventors have found that the above-described piperidinecarboxylic acid amide derivatives can be obtained safely in a high yield under relatively mild conditions by reacting a 2-oxazoline compound with a piperidine derivative, which is a precursor of the intended compound, in the presence of an acid. The present invention has been completed on the basis of this finding.

Namely, the present invention provides a process for producing piperidinecarboxylic acid amide derivatives of general formula (9), which comprises the step of reacting a 2-oxazoline compound of general formula (1) with a piperidine derivative of general formula (2) or a salt thereof in the presence of an acid:

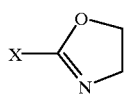
(1)

wherein X represents a heterocyclic ring which may have a substituent, an alkyl group having 1 to 10 carbon atoms, which may have a substituent, an alkoxyl group having 1 to 10 carbon atoms, which may have a substituent, a cycloalkyl group having 3 to 10 carbon atoms, which may have a substituent, an alkenyl group having 2 to 10 carbon atoms, which may have a substituent, an aralkyl group having 7 to 12 carbon atoms and having an alkyl moiety having 1 to 6 carbon atoms, which may have a substituent, or phenyl group

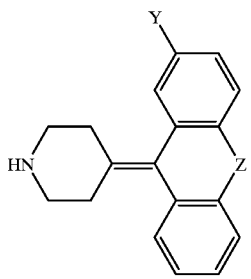
(2)

wherein Y represents hydrogen atom or a halogen atom, and Z represents an organic group of any of the following formulae (3), (4), (5), (6), (7) and (8),

—CH=CH— (3)

—S—CH₂— (4)

—O—CH₂— (5)

—S— (6)

—O— (7)

—CH₂—CH₂— (8)

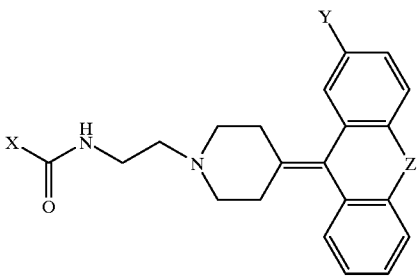
(9)

wherein X, Y and Z are as defined above.

The present invention also provides piperidinecarboxylic acid amide derivatives of the following general formula (10):

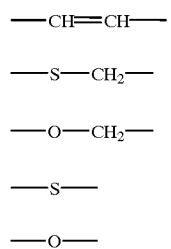
(10)

BEST MODE FOR CARRYING OUT THE INVENTION

X in general formula (1) for the 2-oxazoline compounds used in the present invention is a heterocyclic ring which may have a substituent, an alkyl group having 1 to 10 carbon atom, which may have a substituent, an alkoxyl group having 1 to 10 carbon atom, which may have a substituent, a cycloalkyl group having 3 to 10 carbon atom, which may have a substituent, an alkenyl group having 2 to 10 carbon atom, which may have a substituent, or an aralkyl group having 7 to 12 carbon atoms and having an alkyl moiety having 1 to 6 carbon atoms, which may have a substituent, or phenyl group.

The heterocyclic rings include, for example, pyridyl, piperidyl, piperidino, morpholinyl, morpholino, thiomorpholinyl, thiomorpholino, piperazyl, thienyl and furyl groups.

The alkyl groups having 1 to 10 carbon atoms may be either linear or branched, and they include, for example, methyl, ethyl, propyl, butyl, pentyl, hexyl, heptyl, octyl, nonyl and decyl groups.

The alkoxyl groups having 1 to 10 carbon atoms may be either linear or branched, and they include, for example, methoxyl, ethoxyl, propoxyl, butoxyl, pentyloxy, hexyloxy, heptyloxy and octyloxy groups.

The cycloalkyl groups having 3 to 10 carbon atoms include, for example, cyclopropyl, cyclobutyl, cyclopentyl, cyclohexyl, cycloheptyl, cyclooctyl, cyclononyl and cyclodecyl groups.

The alkenyl groups having 2 to 10 carbon atoms may be either linear or branched, and they include, for example, ethylene, propylene, butene, pentene, hexene, heptene, octene, nonene and decene groups.

In the aralkyl groups having 7 to 12 carbon atoms and also having an alkyl moiety having 1 to 6 carbon atoms, the alkyl moiety may be either linear or branched. They include, or example, phenylmethyl, phenylethyl, phenylpropyl, henylbutyl, phenylpentyl and phenylhexyl groups.

These groups X may be either substituted or substituted. When X is a phenyl group, heterocyclic group or cycloalkyl group, the substitution position on the ring is not particularly limited, and the substituent may be any of the above-described alkyl, alkoxyl and alkenyl groups.

2-Oxazoline compounds of general formula (1) can be easily produced by, for example, a process described in Journal of American Chemical Society (J. Am. Chem. Soc.), Vol. 82, p. 2032 (1960). For example, 2-(1-formyl-4-piperidino)-2-oxazoline can be produced by reacting an amido compound (prepared from 1-formylisonipecotic acid and 2-aminoethanol) with p-toluenesulfonyl chloride under basicconditions. 2-Methyl-4,5-dihydo-1,3-oxazole of general formula (1) wherein X is methyl group and 2-ethyl-4,5-dihydo-1,3-oxazole of general formula (1) wherein X is ethyl group are easily available on the market on relatively low cost.

In general formula (2) for the piperidine derivatives used in the present invention, Y represents hydrogen atom or a halogen atom, and Z represents an organic group of any of following formulae (3) to (8):

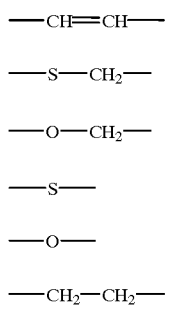

The piperidine derivatives of general formula (2) are known compounds described in Journal of Medicinal Chemistry, Vol. 8, p. 829 (1965) and J. P. KOKAI Nos. Sho 50-18478, Hei 3-12835, Hei 5-208976, etc. They can be easily produced by methods described in J. P. KOKAI Nos. Hei 3-128354 and Hei 5-208976. For example, 4-(5H--dibenzo[a,d]cycloheptene-5-ylidene)-1-piperidine can be obtained by reacting 4-(5H-dibenzo[a,d]cycloheptene-5-ylidene)-1-methylpiperidine with ethyl chloroformate or the like to replace the methyl group with ethoxycarbonyl group or the like and then eliminating the ethoxycarbonyl group or the like with, for example, potassium hydroxide.

As for the acids usable in the present invention, the Lewis acids include, for example, $BF.(CH_3CH_2)_2O$ and zinc chloride, and the proton acids include, for example, p-toluenesulfonic acid, methanesulfonic acid, sulfuric acid and nitric acid. Among them, p-toluenesulfonic acid or its hydrate is the most preferred for inhibiting the production of by-products and for obtaining the intended product in a high yield. The amount of the acid used herein is in a relatively wide range. It is preferably 3 to 75 molar %, more preferably 4 to 70 molar %, still more preferably 6 to 60 molar %, further preferably 5 to 50 molar %, particularly preferably 8 to 25 molar %, and most preferably 10 to 17 molar %. When it is smaller than 5 molar %, the reaction yield is lowered and, on the contrary, more than 100 molar % of the acid is economically not preferred and the reaction yield is lowered in such a case.

The reaction temperature in the present invention, which varies depending on the kind of the starting materials, kind of the solvent and other conditions, is usually 50 to 140° C., preferably 70 to 130° C. and still preferably 80 to 125° C. At a high temperature of above 140° C., a pressure vessel is necessitated because of the gasification of the starting materials and solvent and, on the contrary, a temperature of below 50° C. is not preferred for conducting the reaction on an industrial scale because the reaction rate is seriously lowered.

The reaction solvents usable in the present invention include halogenated hydrocarbons such as chloroform and carbon tetrachloride; aromatic hydrocarbons such s benzene, toluene and xylene; and hydrocarbons such as heptane and hexane. Water and alcohols are not preferred because they cause the decomposition of 2-oxazoline. The reaction can be conducted without any solvent.

The reaction product obtained by the process of the present invention is isolated and purified in the form of the free compound or a salt thereof. The isolation/purification can be conducted by the extraction, concentration, distillation, crystallization and various chromatographic methods.

Some of the piperidinecarboxylic acid amide derivatives of general formula (9) produced by the process of the present invention are known to be usable as the serotonin antagonists or antithrombocytic agents according to, for example, J. P. KOKAI No. Hei 8-3135. For example, J. P. KOKAI No. Hei 8-3135 discloses compounds of general formula (9) wherein Y is either hydrogen atom or a halogen atom, Z is an organic group of any of following formulae (3), (4), (6) and (8):

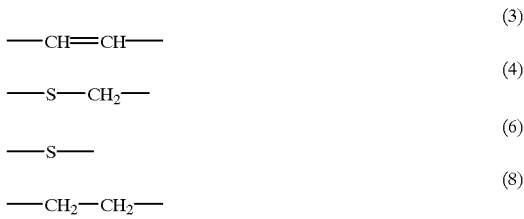

and X is a heterocyclic ring which may have a substituent (preferably pyridyl, piperidyl, piperidino, morpholinyl, morpholino, thiomorpholinyl, thiomorpholino or piperazyl group which may have a substituent), an alkyl group having 1 to 8 carbon atoms and a substituent, a cycloalkyl group having 4 to 8 carbon atoms and a substituent, or an alkoxyl group having 1 to 8 carbon atoms which may have a substituent. According to J. P. KOKAI No. Hei 8-3135, the substituent of X is preferably a substituent of either following formula (11) or (12):

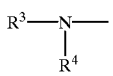
(12)

wherein R² represents a hydrogen atom, an alkyl or alkoxyl group having 1 to 6 carbon atoms, or an amino or acylaminoalkyl group which may be substituted with an alkyl group, and R³ and R⁴, which may be the same or different from each other, each represent a hydrogen atom, an alkyl, acyl or alkoxycarbonyl group having 1 to 6 carbon atoms, or an aminocarbonyl group which may be substituted with an alkyl group.

Examples of the substituents of X include formyl, acetyl, propionyl, butyryl, isobutyryl, valeryl, isovaleryl, pivaloyl, carbamoyl, N-methylcarbamoyl, N-ethylcarbamoyl, N-propylcarbamoyl, N,N-dimethylcarbamoyl, N-formylglycyl, N-acetylglycyl, N-formyl-β-alanyl, N-acetyl-β-alanyl, N-methyl-N-formyl, N-methyl-N-acetyl, N-methyl-N-propionyl, N-ethyl-N-formyl and N-ethyl-N-acetyl groups.

When Z is an organic group of formula (5) or (7) and X is an alkenyl group having 2 to 10 carbon atoms and a substituent, an aralkyl group having 7 to 12 carbon atoms, a substituent and an alkyl moiety having 1 to 6 carbon atoms, or phenyl group, examples of the substituents of X are the same as those described above.

The compounds which per se are known to be usable as the serotonin antagonists or antithrombocytic agents as described above can be easily produced by the one-step reaction according to the process of the present invention.

On the other hand, piperidinecarboxylic acid amides of above general formula (9), but which are different from those described above, are useful as intermediates for the serotonin antagonists or antithrombocytic agents. Namely, compounds of above general formula (9) wherein X represents a substituent-free alkyl group having 1 to 10 carbon atoms, a substituent-free cycloalkyl group having 3 to 10 carbon atoms, a substituent-free alkenyl group having 2 to 10 carbon atoms, a substituent-free aralkyl group having 7 to 12 carbon atoms and an alkyl moiety having 1 to 6 carbon atoms, or phenyl group (preferably a substituent-free alkyl group having 1 to 10 carbon atoms, particularly preferably, a substituent-free alkyl group having 1 to 3 carbon atoms) are usable as the intermediates for the serotonin antagonists or antithrombocytic agents. When such a compound is used as the intermediate, a piperidinecarboxylic acid amide derivative of general formula (9) is hydrolyzed with an acid, such as 10% aqueous sulfuric acid solution, to obtain a compound of general formula (13), and this compound is condensed with a carboxylic acid derivative of X such as 1-formylisonicopetic acid (14) to obtain a piperidinecarboxylic acid amide derivative, such as that represented by general formula (15), useful as the serotonin antagonist or antithrombocytic agent.

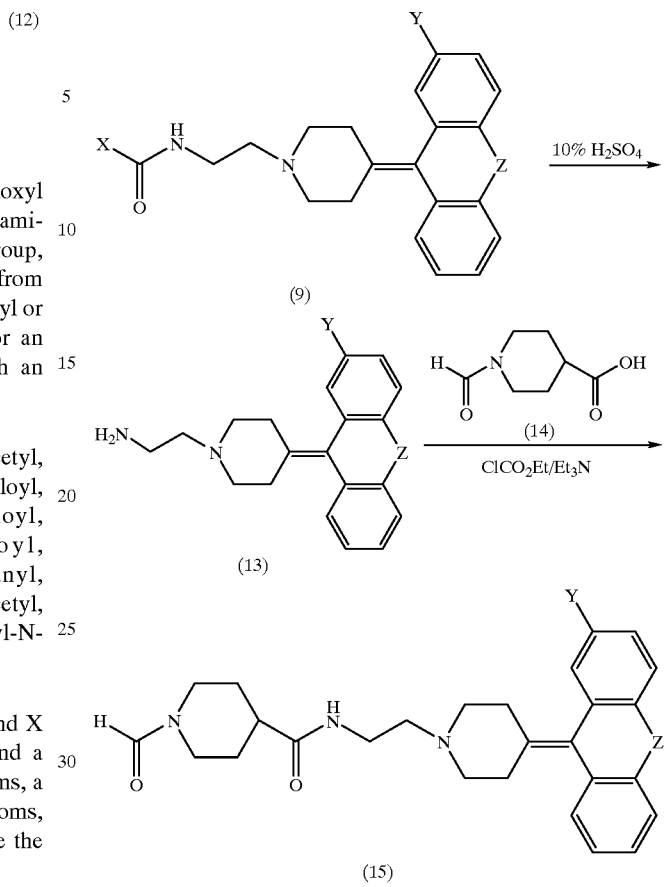

Wherein X, Y and Z are as defined above.

When the intended product is obtained via the intermediate as described above, the intermediate is particularly preferably a piperidinecarboxylic acid derivative of following general formula (10) because they can be easily synthesized from 2-oxazoline compounds available on the market:

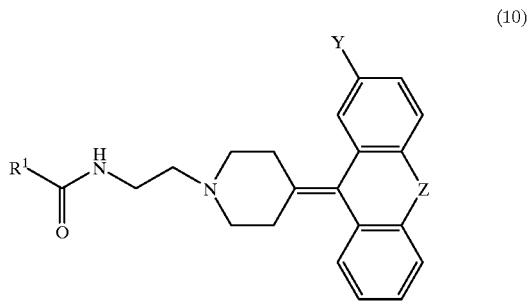

Wherein R¹ represents methyl or ethyl group, and Y and Z are as defined above.

In the production of the piperidinecarboxylic acid amide derivatives included in the compounds of general formula (9) and useful as the serotonin antagonists or antithrombocytic agents, the method of producing the intended compound can be suitably selected from two methods, i.e. the above-described method wherein substituent X is introduced through the intermediate, and the method wherein substituent X is previously introduced into the 2-oxazoline compound and the intended product is directly produced by the one-step reaction.

In the present invention, piperidinecarboxylic acid amide derivative of general formula (9) usable as the serotonin antagonist or antithrombocytic agent is produced by the one-step reaction, then this derivative can be used as an intermediate and another substituent is introduced thereinto by the above-described method to obtain a serotonin antagonist or antithrombocytic agent having another function.

EXAMPLES

The following Examples will further illustrate the present invention, which by no means limit the invention.

Referential Example 1

Production of 2-(1-formyl-4-piperidino)-2-oxazoline 100 ml of toluene was added to 5.02 g (32.0 mmol) of 1-formylisonipecotic acid. 2.8 ml (38.4 mmol) of thionyl chloride and 0.1 ml of N,N-dimethylformamide were added to the resultant mixture at 45° C., and they were stirred at 60° C. for 30 minutes to obtain an acid chloride.

100 ml of acetonitrile, 14.7 ml (105.6 mmol) of triethylamine and the acid chloride obtained as described above were successively added in this order to 1.95 g (32.0 mmol) of 2-aminoethanol at 30° C., and the obtained mixture was stirred for 3 hours. An insoluble matter was filtered out, and the filtrate was concentrated to obtain an oil.

The oil thus obtained was dissolved in 70 ml of acetonitrile and 70 ml of toluene. 6.10 g (32.0 mmol) of p-toluenesulfonyl chloride and 10.12 g (128.0 mmol) of pyridine were added to the solution, and the resultant mixture was stirred at −30° C. for one hour and then under heating under reflux overnight. 35 ml of acetonitrile was added to the reaction liquid, After filtering out an insoluble matter, the filtrate was concentrated. The obtained oil was purified by the silica gel column chromatography (chloroform:methanol=9:1) to obtain 2.45 g (13.4 mmol) of the title compound (yield: 42%).

1H NMR (CDCl$_3$)

1.7 ppm (2H, m: piperidine ring CH$_2$)
2.0 ppm (2H, m: piperidine ring CH$_2$)
2.6 ppm (1H, m: piperidine ring CH)
2.9 ppm (1H, m: piperidine ring CH$_2$)
3.2 ppm (1H, m: piperidine ring CH$_2$)
3.7 ppm (1H, m: piperidine ring CH$_2$)
3.9 ppm (2H, t: oxazoline ring CH$_2$)
4.3 ppm (2H, t: oxazoline ring CH$_2$)
4.3 ppm (1H, m: piperidine ring CH$_2$)
8.1 ppm (1H, s: formyl group CHO)
MS (ESI) calculated: C$_9$H$_{14}$N$_2$O$_2$(M$^+$) 183, found: 183.

Example 1

Production of N-[2-[4-(5H-dibenzo[a,d] cycloheptene-5-ylidene)piperidino]ethyl]-1-formyl-4-piperidinecarboxylic acid amide 0.50 g (2.7 mmol) of 2-(1-formyl-4-piperidino)-2-oxazoline, 12 ml of toluene, 0.50 g (1.8 mmol) of 4-(5H-dibenzo [a,d]cycloheptene-5-ylidene)-1-piperidine and 0.35 g (1.8 mmol) of p-toluenesulfonic acid monohydrate were stirred under heating and reflux overnight. The solvent was distilled off. To the residue was added a solution comprising 6 ml of acetonitrile, 18 ml of water and 0.2 ml of 6 M aqueous sodium hydroxide solution and seed crystal. Crystals thus formed were cooled and taken by the filtration and then dried under reduced pressure to obtain 0.53 g of the title compound (yield: 65%).

1H NMR (CDCl$_3$)

1.5 ppm–2.6 ppm [15H, m: ethylene chain CH$_2$, piperidine ring, piperidine ring (isonipecotic acid)]
2.7 ppm [1H, m: piperidine ring (isonipecotic acid)]
3.1 ppm [1H, d: piperidine ring (isonipecotic acid)]
3.3 ppm (2H, q: ethylene chain CH$_2$)
3.7 ppm [1H, d: piperidine ring (isonipecotic acid)]
4.4 ppm [1H, d: piperidine ring (isonipecotic acid)]
6.2 ppm (1H, br: amide NH)
6.9 ppm (2H, s: cycloheptene ring double bond CH)
7.3 ppm (8H, m: benzene ring CH)
8.0 ppm (1H, s: formyl group CHO)
MS (ESI) calculated: C$_{29}$H$_{33}$N$_3$O$_2$(M$^+$)456, found 456.

Example 2

Production of N-[2-[(4,5H-dibenzo[a,d] cycloheptene-5-ylidene)piperidino]ethyl]acetamide 52.8 g (193 mmol) of 4-(5H-dibenzo[a,d]cycloheptene-5-ylidene)-1-piperidine, 25.0 ml (289 mmol) of 2-methyl-2-oxazoline and 7.34 g (38.6 mmol) of p-toluenesulfonic acid monohydrate were heated under reflux in toluene (185 ml) for 6 hours. The reaction liquid was cooled. 640 ml of toluene, 405 ml of water and 9.7 ml of 6 M aqueous sodium hydroxide solution were added to the reaction liquid to conduct the extraction at 75° C., and the aqueous layer was removed. The organic layer was washed with 162 ml of water twice. After the seeding at 65° C., the obtained mixture was cooled to 10° C. Crystals thus obtained were taken by the filtration and dried under reduced pressure to obtain 64.3 g (179 mml) of the title compound (yield: 93%).

1H NMR (CDCl$_3$)

2.0 ppm (3H, s: acetyl group CH$_3$)
2.1 ppm (4H, m: piperidine ring CH$_2$)
2.3 ppm (1H, m: piperidine ring CH$_2$)
2.4 ppm (1H, t: ethylene chain CH$_2$)
2.5 ppm (2H, m: piperidine ring CH$_2$)
3.3 ppm (2H, m: ethylene chain CH$_2$)
6.1 ppm (1H, br: amide NH)
6.9 ppm (2H, s: cycloheptene ring double bond CH)
7.2 ppm (8H, m: benzene ring CH)
MS (ESI) calculated: C$_{24}$H$_{26}$N$_2$O (M$^+$) 359, found: 359.

Referential Example 2

Production of N-2-(4-(5H-dibenzo[a,d] cycloheptene-5-ylidene)piperidino)ethylamine 560 ml of water and 62 ml of 95% sulfuric acid were added to 57.4 g (160 mmol) of N-2-[(4-5H-dibenzo[a,d] cycloheptene-5-ylidene)piperidino]ethyl]acetamide, and the resultant mixture was heated under reflux for 6 hours. The reaction liquid was cooled and then neutralized with 410 ml of 6 M aqueous sodium hydroxide solution. The crystals thus formed were dissolved in 622 ml of toluene. The aqueous layer was removed to obtain a solution containing 49.0 g (155 mmol) of the title compound in toluene (yield: 96.5%).

1H NMR (CDCl$_3$)

1.4 ppm (2H, br: amine NH$_2$)
2.1 ppm (4H, m: piperidine ring CH$_2$)

2.3 ppm (4H, m: ethylene chain CH$_2$, piperidine ring CH$_2$)
2.6 ppm (2H, m: piperidine ring CH$_2$)
2.7 ppm (2H, m: ethylene chain CH$_2$)
6.9 ppm (2H, s: cycloheptene ring double bond CH)
7.3 ppm (8H, m: benzene ring CH)
MS (ESI) calculated: C$_{22}$H$_{24}$N$_2$ (M$^+$) 317, found: 317.

Referential Example 3

Production of N-2-[(4-(5H-dibenzo[a,d] cycloheptene-5-ylidene)piperidino)ethyl]-1-formyl-4-piperidinecarboxylic acid amide 17.4 ml (182 mmol) of ethyl chloroformate was added to a suspension of 28.7 g (182 mmol) of 1-formylisonipecotic acid in toluene. 25.4 ml (182 mmol) of triethylamine was dropped into the resultant mixture at 5° C., and they were stirred for one hour. 327 g of a solution (concentration: 15%, 155 mmol) of N-2-(4-(5H-dibenzo[a,d]cycloheptene-5-ylidene)piperidino)ethylamine in toluene was dropped into the obtained liquid mixture, and they were stirred for one hour. After the extraction with water of pH 3, the organic layer was removed. pH was adjusted to 7. After the extraction with ethyl acetate, the aqueous layer was removed. The organic layer was heated and then cooled to precipitate crystals, which were taken by the filtration. After drying under reduced pressure, 59.1 g (134 mmol) of the title compound was obtained (yield: 86.5%).

Example 3

Production of N-2-[(4-(5H-dibenzo[a,d] cycloheptene-5-ylidene)piperidino)ethyl]acetamide 1.36 g (5.0 mmol) of 4-(5H-dibenzo[a,d]cycloheptene-5-ylidene)-1-piperidine, 0.84 ml (10.0 mmol) of 2-methyl-2-oxazoline and 0.61 ml (5.0 mmol) of boron trifluorode etherate were heated under reflux in toluene (10 ml) for three hours. The reaction liquid was cooled. After the extraction with 30 ml of dichloromethane and 40 ml of saturated aqueous sodium hydrogencarbonate solution at 75° C., the aqueous layer was removed. The organic layer was concentrated to dryness to obtain 1.24 g (3.5 mmol) of the crystallized title compound (yield: 69%).

Referential Example 4

N-2-[(4-(5H-dibenzo[a,d]cycloheptene-5-ylidene) piperidino)ethyl]-1-formyl-4-piperidinecarboxyic acid amide was obtained from the compound obtained in Example 3 in the same manner as that of Referential Examples 2 and 3.

Example 4

Production of N-2-[(4-(5H-dibenzo[a,d] cycloheptene -5-ylidene)piperidino)ethyl] propionamide 13.7 g (50.0 mmol) of 4-(5H-dibenzo[a,d]cycloheptene-5-ylidene)-1-piperidine, 7.6 ml (75.0 mmol) of 2-ethyl-2-oxazoline and 1.90 g (10.0 mmol) of p-toluenesulfonic acid monohydrate were heated under reflux in toluene (50 mol) for 6 hours. The reaction liquid was cooled. After the extraction with 15 ml of water and 15 ml of 1 M aqueous sodium hydroxide solution, the aqueous layer was removed. The organic layer was washed with 30 ml of water twice. After the inoculation at 65° C., the product was cooled to 10° C. The crystals thus precipitated were taken by the filtration and dried under reduced pressure to obtain 17.1 g (44.5 mmol) of the title compound (yield: 89%).

1H NMR (CDCl$_3$)

1.1 ppm (3H, t: ethyl group CH$_3$)
2.1 ppm (4H, m: piperidine ring CH$_2$)
2.2 ppm (2H, q: ethyl group CH$_2$)
2.3 ppm (2H, m: piperidine ring CH$_2$)
2.4 ppm (2H, t: ethylene chain CH)
2.5 ppm (2H, m: piperidine ring CH$_2$)
3.3 ppm (2H, m: ethylene chain CH$_2$)
6.1 ppm (1H, br: amide NH)
6.9 ppm (2H, s: cycloheptene ring double bond CH)
7.2 ppm (8H, m; benezene ring CH)
MS (ESI) calculated: C$_{25}$H$_{28}$N$_2$O (M$^+$)373, found: 373.

Referential Example 5

N-2-[(4-(5H-dibenzo [a,d]cycloheptene-5-ylidene) piperidino)ethyl]1-formyl-4-piperidinecarboxyic acid amide was obtained from the compound obtained in Example 4 in the same manner as that of Referential Examples 2 and 3.

According to the present invention, piperidinecarboxylic acid amide derivatives usable as serotonin antagonists, anti-thrombocytic agents or intermediates therefor can be obtained in a high yield under safe, relatively mild conditions.

What is claimed is:

1. A process for producing a piperidinecarboxylic acid amide derivative represented by formula (9):

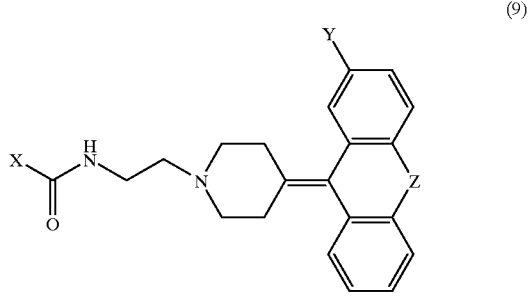

(9)

wherein

X represents an alkyl group having 1 to 2 carbon atoms;

Y represents a hydrogen atom; and

Z represents a CH=CH— group comprising:

reacting a 2-oxazoline compound represented by formula (1):

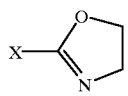

(1)

wherein X is as defined above, with a piperidine derivative represented by formula (2):

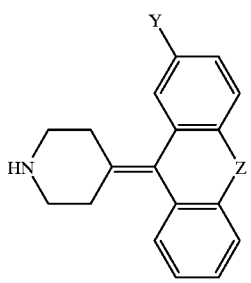

(2)

wherein Y and Z are as defined above,
or a salt thereof, in the presence of an acid.

2. The process of claim 1, wherein X is a methyl group.

3. The process of claim 1, wherein the acid is selected from the group consisting of boron trifluorode etherate, zinc chloride, p-toluenesulfonic acid, a hydrate thereof and methanesulfonic acid.

4. The process of claim 3, wherein the acid is selected from the group consisting of p-toluenesulfonic acid, a hydrate thereof and boron trifluorode etherate.

5. The process of claim 4, wherein p-toluenesulfonic acid or a hydrate thereof is used in an amount of 8 to 25 molar % based on the 2-oxazoline compound.

6. The process of claim 1, wherein the reaction is conducted in a solvent.

7. The process of claim 6, wherein the solvent is selected from the group consisting of halogenated hydrocarbons, aromatic hydrocarbons and hydrocarbons.

8. The process of claim 1, wherein the reaction is conducted without any solvent.

9. The process of claim 1, wherein the reaction is conducted at a temperature of 50 to 140° C.

10. The process of claim 1, wherein X is a methyl group, the acid is selected from the group consisting of p-toluenesulfonic acid, a hydrate thereof and boron trifluorode etherate, and the reaction is conducted at a temperature of 50 to 140° C.

11. The process of claim 10, wherein the reaction is conducted in a solvent.

12. The process of claim 11, wherein the solvent is selected from the group consisting of halogenated hydrocarbons, aromatic hydrocarbons, and hydrocarbons.

13. The process of claim 10, wherein the reaction is conducted without any solvent.

14. The process of claim 1, which further comprises isolating the resulting piperidinecarboxylic acid amide derivative.

15. The process of claim 1, which further comprises isolating the piperidinecarboxylic acid amide derivative and purifying the piperidinecarboxylic acid amide derivative in the form of free acid or a salt thereof.

* * * * *